United States Patent
Pleschke et al.

(10) Patent No.: US 9,920,002 B2
(45) Date of Patent: Mar. 20, 2018

(54) METHODS FOR PRODUCING SULFONIC ACID DIAMIDES

(75) Inventors: Axel Pleschke, Mannheim (DE);
Thomas Schmidt, Neustadt (DE);
Joachim Gebhardt, Wachenheim (DE);
Sandra Loehr, Ludwigshafen (DE);
Michael Keil, Freinsheim (DE); Jan Hendrik Wevers, Hohen-Suelzen (DE)

(73) Assignee: BASF SE, Ludwigshafen (DE)

( * ) Notice: Subject to any disclaimer, the term of this patent is extended or adjusted under 35 U.S.C. 154(b) by 184 days.

(21) Appl. No.: 12/681,843

(22) PCT Filed: Oct. 10, 2008

(86) PCT No.: PCT/EP2008/063630
§ 371 (c)(1),
(2), (4) Date: Apr. 6, 2010

(87) PCT Pub. No.: WO2009/050120
PCT Pub. Date: Apr. 23, 2009

(65) Prior Publication Data
US 2010/0222586 A1    Sep. 2, 2010

(30) Foreign Application Priority Data

Oct. 12, 2007  (EP) .................... 07118416

(51) Int. Cl.
| C07C 303/34 | (2006.01) |
| C07C 307/06 | (2006.01) |
| C07D 239/54 | (2006.01) |
| A01N 43/54 | (2006.01) |
| C07C 381/00 | (2006.01) |

(52) U.S. Cl.
CPC ............ *C07C 303/34* (2013.01); *A01N 43/54* (2013.01); *C07C 307/06* (2013.01); *C07C 381/00* (2013.01); *C07D 239/54* (2013.01)

(58) Field of Classification Search
CPC .... C07C 303/34; C07C 307/06; C07D 239/54
USPC .................. 564/80, 84, 90, 95, 79; 544/309
See application file for complete search history.

(56) References Cited

U.S. PATENT DOCUMENTS

| 3,198,785 | A | 8/1965 | Houlihan |
| 3,709,677 | A * | 1/1973 | Houlihan ..................... 504/248 |
| 3,962,326 | A | 6/1976 | Semler et al. |
| 4,308,216 | A | 12/1981 | Freitag et al. |
| 4,382,898 | A | 5/1983 | Rudolph et al. |
| 5,017,211 | A | 5/1991 | Wenger et al. |
| 5,238,908 | A | 8/1993 | Lange et al. |
| 5,420,099 | A | 5/1995 | Newton |
| 6,251,829 | B1 | 6/2001 | Li et al. |
| 7,820,846 | B2 | 10/2010 | Hamprecht et al. |
| 7,847,097 | B2 * | 12/2010 | Gebhardt et al. ............ 544/309 |
| 8,124,818 | B2 * | 2/2012 | Loehr et al. .................... 585/19 |
| 8,232,421 | B2 | 7/2012 | Hamprecht et al. |
| 8,541,611 | B2 | 9/2013 | Hamprecht et al. |
| 2005/0159622 | A1 | 7/2005 | Hamprecht et al. |
| 2006/0004220 | A1 | 1/2006 | Hamprecht et al. |
| 2008/0033174 | A1 | 2/2008 | Lohr et al. |
| 2010/0228054 | A1 | 9/2010 | Keil et al. |
| 2012/0310010 | A1 | 12/2012 | Schmidt et al. |

FOREIGN PATENT DOCUMENTS

| DE | 1240853 | 5/1967 |
| EP | 1 516 870 | 3/2005 |
| JP | 50-30821 | 3/1975 |

(Continued)

OTHER PUBLICATIONS

Vandi et al. J. Org. Chem., vol. 26, No. 4, (1961), pp. 1136-1138.*

(Continued)

*Primary Examiner* — Venkataraman Balasubramanian
(74) *Attorney, Agent, or Firm* — Brinks Gilson & Lione

(57) ABSTRACT

The present invention relates to a process for preparing sulfuric diamides of the general formula I $$R^1R^2N\text{—}S(O)_2\text{—}NH_2 \qquad (I)$$

in which $R^1$ and $R^2$ are each independently a primary alkyl radical having from 1 to 8 carbon atoms, a secondary alkyl radical having from 3 to 8 carbon atoms or a cycloalkyl radical having from 5 to 8 carbon atoms, or, together with the nitrogen atom, form a 5- to 8-membered, saturated nitrogen heterocycle which, as well as the nitrogen atom, may have a further heteroatom selected from O and S as a ring member, where the nitrogen heterocycle is unsubstituted or may have 1, 2, 3 or 4 alkyl groups having in each case from 1 to 4 carbon atoms as substituents. The process comprises the following steps:

i) the reaction of a secondary amine of the formula II $$R^1R^2NH \qquad (II)$$

in which $R^1$ and $R^2$ are each as defined above with sulfuryl chloride in an inert solvent, especially an aromatic solvent, in the presence of a tertiary amine to give a sulfamoyl chloride of the formula III $$R^1R^2N\text{—}S(O)_2\text{—}Cl \qquad (III)$$

in which $R^1$ and $R^2$ are each as defined above, and ii) reaction of the sulfamoyl chloride of the formula III obtained in step i) with ammonia, the sulfamoyl chloride of the formula III being used in step ii) in the form of the solution obtained in step i) in the inert solvent, especially the aromatic solvent.

9 Claims, No Drawings

(56) References Cited

FOREIGN PATENT DOCUMENTS

| JP | 56-30945 | 3/1981 |
|---|---|---|
| JP | 57-99553 | 6/1982 |
| JP | 61-155350 | 7/1986 |
| JP | 5-279210 | 10/1993 |
| JP | 2001/523222 | 11/2001 |
| JP | 2003-519130 | 6/2003 |
| JP | 2004-501084 | 1/2004 |
| JP | 2004-535446 | 11/2004 |
| JP | 2005-501827 | 1/2005 |
| JP | 2005-97138 | 4/2005 |
| JP | 2006-83133 | 3/2006 |
| WO | WO 1989/002891 | 4/1989 |
| WO | WO 98/32748 | 4/1998 |
| WO | WO 01/47897 | 7/2001 |
| WO | WO 01/79203 | 10/2001 |
| WO | WO 2001/083459 | 11/2001 |
| WO | WO 03/002542 | 1/2003 |
| WO | WO 03/007945 | 1/2003 |
| WO | WO 2003/097589 | 11/2003 |
| WO | WO 2004/035545 | 4/2004 |
| WO | WO 2004/039768 | 5/2004 |
| WO | WO 2004/106324 | 12/2004 |
| WO | WO 2006/010474 | 2/2006 |
| WO | WO 2006/090210 | 8/2006 |
| WO | WO 2007063028 | 6/2007 |

OTHER PUBLICATIONS

Wheeler et al. J. Am. Chem. Soc., vol. 66, (1944), pp. 1242-1243.*
Adkison et al., "Semicarbazone-Based Inhibitors of Cathepsin K, Are They Prodrugs for Aldehyde Inhibitors," Bioorganic and Medicinal Chemistry Letters, vol. 16, No. 4, (2006), pp. 978-983. XP002474074.
Audrieth et al., "Hydrazides of Sulfuric Acid and Their Derivatives. II. The Sulfamyl Hydrazides," J. Org. Chem., vol. 21, No. 4, (1956), pp. 426-428. XP002474073.
Beckert et al., "Elecktrophile Aromatische Substitution," Organikum, $22^{nd}$ ed., (2004), pp. 358-361.
Beckert et al., "Reaktionen von Carbonylverbindungen," Organikum, $22^{nd}$ ed., (2004), pp. 496-499.
Behrend, "Über die Einwirkung von Sulfurylchlorid auf secundäre Aminbasen," Justus Liebigs Annalen Der Chemie, vol. 222, (1884), pp. 116-136. XP002474075.
Binkley ed Degering, "Organic Synthesis with Sulfuryl Chloride," J. Am. Chem. Soc., vol. 61, (1939), pp. 3250-3251. XP002474072.
Hamprecht et al., "Alkylsulfanmidsäurechloride als Schlüsselbausteine für Neue Pflanzenschutzwirkstoffe," Agnew. Chem., vol. 93, (1981), pp. 151-163.
International Preliminary Report on Patentability, issued in PCT/EP2008/063630, dated May 11, 2010.
International Search Report, issued in PCT/EP2008/063630, dated Jan. 30, 2009.
Scherer et al., "Reaktionen mit Benzotrichlorid und Pentachloräthyl-Benzol," Justus Liebigs Annalen der Chemie, vol. 677, (1964), pp. 83-95.
Unterhalt, "Schwefesäure-di-N-Derivative," in Methoden der Organischen Chemie [Methods of Organic Chemistry], Houben-Weyl ed., E11, (1985), pp. 1019-1025.
Vandi et al., "Synthesis and Properties of Some N-Substituted Sulfamides," J. Org. Chem., vol. 26, No. 4, (1961), pp. 1136-1138. XP002474071.
Wheeler et al., "Preparation and Properties of Certain Derivatives of Sulfamide," J. Am. Chem. Soc., vol. 66, (1944), pp. 1242-1243.

* cited by examiner

METHODS FOR PRODUCING SULFONIC ACID DIAMIDES

This application is a National Stage application of International Application No. PCT/EP2008/063630 filed Oct. 10, 2008, the entire contents of which is hereby incorporated herein by reference. This application also claims the benefit under 35 U.S.C. § 119 of European Patent Application No. 07118416.2, filed Oct. 12, 2007, the entire contents of which is hereby incorporated herein by reference.

The present invention relates to a process for preparing sulfuric diamides of the general formula I

in which $R^1$ and $R^2$ are each independently a primary alkyl radical having from 1 to 8 carbon atoms, a secondary alkyl radical having from 3 to 8 carbon atoms or a cycloalkyl radical having from 5 to 8 carbon atoms, or, together with the nitrogen atom, form a 5- to 8-membered, saturated nitrogen heterocycle which, as well as the nitrogen atom, may have a further heteroatom selected from O and S as a ring member, where the nitrogen heterocycle is unsubstituted or may have 1, 2, 3 or 4 alkyl groups having in each case from 1 to 4 carbon atoms as substituents.

Sulfuric diamides of the formula I are interesting intermediates for the preparation of active ingredients, for example for the preparation of the active herbicidal ingredients described in WO01/83459.

Processes for preparing sulfuric diamides of the formula I have been known in principle for some time. For instance, R. Behrend, J. Liebigs Ann. Chem. 1884, 222, p. 116-136 describes the preparation of dimethylaminosulfonamide and diethylaminosulfonamide by successive reaction of sulfuryl chloride ($SO_2Cl_2$) with diethylammonium chloride or diethylammonium chloride and subsequent reaction of the resulting dimethylamido-sulfuryl chloride or diethylamidosulfuryl chloride with gaseous ammonia. However, the reaction proceeds only incompletely. Also disadvantageous is the hydrogen chloride released in the first step.

K. W. Wheeler et al., J. Am. Chem. Soc. 1944, 66, p. 1242, describe the preparation of tri- and tetrasubstituted sulfo diamides, in which, in a first step, two equivalents of a secondary amine are first reacted with sulfuryl chloride in substance and the resulting sulfamyl chloride is reacted with two equivalents of a further amine. The yields of this process are unsatisfactory.

WO01/83459 describes the preparation of sulfuric diamides of the general formula I by reaction of chlorosulfonamide with a primary or secondary amine. The chlorosulfonamide is prepared by hydrolysis of chlorosulfonyl isocyanate. Chlorosulfonyl isocyanate is, however, comparatively costly.

WO03/097589, in turn, describes the preparation of sulfuric diamides of the general formula I, in which, in a first step, the chlorosulfonamide of a primary or secondary amine is prepared by successive reaction of the primary or secondary amine with sulfur trioxide in the presence of a tertiary amine, followed by the reaction of the resulting ammonium salt of the corresponding amidosulfonic acid with phosphorus halide. Subsequently, the resulting chlorosulfonamide, also referred to hereinafter as sulfamoyl chloride, is reacted with ammonia. The process is notable for better yields, but is comparatively complicated owing to the multitude of steps.

It is thus an object of the present invention to provide an easily performable process for preparing sulfuric diamides of the general formula I designated above, which provides these compounds in good yields and which can be carried out with inexpensive starting materials. This object is surprisingly achieved by the process defined hereinafter.

The present invention provides a process for preparing sulfuric diamides of the general formula I designated above, comprising the following steps:

i) the reaction of a secondary amine of the formula II

in which $R^1$ and $R^2$ are each as defined above with sulfuryl chloride in an inert solvent, especially an aromatic solvent, in the presence of a tertiary amine to give a sulfamoyl chloride of the formula III

in which $R^1$ and $R^2$ are each as defined above, and ii) reaction of the sulfamoyl chloride of the formula III obtained in step i) with ammonia, the sulfamoyl chloride of the formula III being used in step ii) in the form of the solution obtained in step i) in the inert solvent, especially the aromatic solvent.

The process according to the invention is associated with a series of advantages. Firstly, the process according to the invention is comparatively easy to perform. In addition, it affords the desired sulfuric diamides I in good yields, both based on the secondary amine used and on the sulfuryl chloride used. The release of hydrogen chloride is substantially or even completely avoided. The use of expensive starting materials such as chlorosulfonyl isocyanate is not required. The reaction can additionally be handled efficiently on the industrial scale. Moreover, the sulfuric diamides I are obtained in a purity sufficient for further use, and so it requires no complicated purification processes.

In step i) of the process according to the invention, a secondary amine of the formula II, as defined above, is reacted with sulfuryl chloride in an inert solvent, especially an aromatic solvent, in the presence of a tertiary amine. This affords a solution of a sulfamoyl chloride of the formula III, also referred to hereinafter as chlorosulfonamide III.

The tertiary amine serves as an auxiliary base to bind the hydrogen chloride released in the reaction and is used typically in an amount of at least 0.9 equivalent, preferably in an amount of at least 1.0 equivalent, for example in an amount of from 1.0 to 2 equivalents, and especially in an amount of from 1.05 to 1.5 equivalents, based on the secondary amine. The term "equivalents" is equivalent to the term "mole per mole" or "molar equivalents".

The type of tertiary amine is of minor importance for the reaction. Suitable tertiary amines comprise trialkylamines, especially those having from 1 to 6 carbon atoms in the alkyl radicals, N-cycloalkyl-N,N-dialkylamines, especially N-cyclohexyl-N,N-dialkylamines having from 1 to 6 carbon atoms in the alkyl radicals, N,N-dialkylanilines having preferably from 1 to 6 carbon atoms in the alkyl radicals, and also pyridine and quinoline bases.

Examples of suitable tertiary amines are:

from the group of the trialkylamines: trimethylamine, triethylamine, tri-n-propylamine, tri-n-butylamine, dimethylethylamine, dimethyl-n-propylamine, dimethyl-n-butylamine, dimethylisopropylamine, dimethyl-2-butylamine, diethyl-n-propylamine, diethylisopropylamine, diethyl-n-butylamine, tri-n-hexylamine and the like;

from the group of the N-cycloalkyl-N,N-dialkylamines: dimethylcyclohexylamine and diethylcyclohexylamine;

from the group of the N,N-dialkylanilines: dimethylaniline and diethylaniline;
from the group of the pyridine and quinoline bases: pyridine, α-, β- and γ-picoline, quinoline and isoquinoline.

Preferred tertiary amines are trialkylamines and N-cycloalkyl-N,N-dialkylamines, especially tri-$C_1$-$C_6$-alkylamines and N-cyclohexyl-N,N-di-$C_1$-$C_6$-alkylamines. In a particularly preferred embodiment, the tertiary amine used is a tri-$C_1$-$C_6$-alkylamine and especially trimethylamine or triethylamine.

The process according to the invention is suitable in principle for preparing sulfuric diamides of any secondary aliphatic or cyclic amines. Suitable secondary amines can be described by the general formula II. Preference is given to using those secondary amines of the formula II in which the $R^1$ and $R^2$ radicals are bonded to the nitrogen atom via a primary carbon atom ($CH_2$ group) or via a secondary carbon atom (CHR, R=alkyl radical). $R^1$ and $R^2$ may be primary or secondary alkyl radicals having preferably from 1 to 6 or from 3 to 6 carbon atoms, or a cycloalkyl radical having preferably 5 or 6 carbon atoms. $R^1$ and $R^2$ may be the same or different. $R^1$ and $R^2$ may, however, together with the nitrogen atom to which they are bonded, also form a 5-, 6-, 7- or 8-membered, saturated nitrogen heterocycle which, as well as the nitrogen atom, may have a further heteroatom selected from O and S as a ring member and which may optionally be substituted, but the α-carbon atoms (the ring carbon atoms bonded to the nitrogen atom) are preferably unsubstituted or have one substituent.

The expression "primary alkyl radical having from 1 to 8 carbon atoms" represents a saturated linear or branched hydrocarbon radical which has from 1 to 8 and especially from 1 to 6 carbon atoms and is bonded to the nitrogen atom via a $CH_2$ group. Examples of primary alkyl radicals are methyl, ethyl, n-propyl, n-butyl, 2-methylpropyl (isobutyl), n-pentyl, 2-methylbutyl, 3-methylbutyl, n-hexyl, 2-methylpentyl, 3-methylpentyl, 4-methylpentyl, 2-ethylbutyl, etc.

The expression "secondary alkyl radical having from 3 to 8 carbon atoms" represents a saturated acyclic hydrocarbon radical which has from 3 to 8 carbon atoms and is bonded via a secondary carbon atom to the nitrogen atom. Examples of secondary alkyl radicals are 2-propyl (1-methylethyl), 2-butyl, 2-pentyl, 3-pentyl, 2-hexyl, 3-hexyl, 3-methyl-2-butyl, 3-methyl-2-pentyl, 4-methyl-2-pentyl etc.

In a preferred embodiment of the invention, a secondary amine II in which the two $R^1$ and $R^2$ radicals are different alkyl radicals is used. The same applies to the formulae I and III. More particularly, the $R^1$ radical in the formulae I, II and III is a primary alkyl radical having from 1 to 8, in particular having from 1 to 6 and especially having 1 or 2 carbon atoms, or is a secondary alkyl radical having from 3 to 8, in particular from 3 to 6 and especially having 3 or 4 carbon atoms. The $R^2$ radical is especially a secondary alkyl radical having from 3 to 8, in particular from 3 to 6 and especially 3 or 4 carbon atoms. More particularly, $R^1$ is a primary alkyl radical having from 1 to 4 carbon atoms and especially methyl or ethyl, and $R^2$ is a secondary alkyl radical having from 3 to 8, in particular from 3 to 6 and especially 3 or 4 carbon atoms, and is especially isopropyl or 2-butyl. In a very particularly preferred embodiment, a secondary amine of the formula II in which $R^1$ is methyl and in which $R^2$ is a secondary alkyl radical having from 3 to 8, in particular from 3 to 6 and especially 3 or 4 carbon atoms. More particularly, the secondary amine used is N-(1-methylethyl)-N-methylamine ($R^1$=methyl, $R^2$=methylethyl=isopropyl).

The secondary amine of the formula II and the sulfuryl chloride are preferably used in a molar ratio suitable for the stoichiometry of the reaction, which is preferably in the range from 1:1.1 to 1.1:1, in particular in the range from 1:1.05 to 1.05:1 and especially in the range from 1:1.02 to 1.02:1.

According to the invention, step i) proceeds in an inert solvent, especially an aromatic solvent.

An inert solvent is understood to mean an organic solvent which does not enter into any chemical reactions with the reagents, especially with sulfuryl chloride, under the reaction conditions. These include especially aromatic, aliphatic, araliphatic and cycloaliphatic hydrocarbons, and also chlorinated and fluorinated hydrocarbons. Nitrogen-containing and/or oxygen-containing solvents are generally not inert, especially when they have OH or NH groups (so-called protic solvents). The proportion of non-inert solvents in the inert solvent is generally not more than 10% by volume, based on the total amount of the solvent. The inert solvent preferably does not comprise any oxygen-containing and/or nitrogen-containing, aprotic solvents (<1% by volume).

An "aromatic solvent" is understood to mean those solvents whose main constituents are aromatic compounds which are derived from benzene and are liquid at room temperature. Such compounds include, for example, as well as benzene, alkylbenzenes such as toluene, xylenes, trimethylbenzene and ethylbenzene, and also chlorinated and/or fluorinated benzenes such as chlorobenzene, fluorobenzene and dichlorobenzenes.

In addition to these aromatic compounds, the aromatic solvent may also comprise up to 50% by volume, in particular not more than 30% by volume and especially not more than 10% by volume of different inert solvents, for example aliphatic halohydrocarbons, e.g. dichloromethane, trichloromethane and/or dichloroethane, aliphatic or cycloaliphatic hydrocarbons such as n-hexane, n-heptane, octane, cyclohexane, cycloheptane, cyclooctane and mixtures thereof. In addition, the aromatic solvent may also comprise small amounts of non-inert, aprotic oxygen-containing and/or nitrogen-containing solvents, in which case their proportion makes up preferably not more than 10% by volume, based on the total amount of the solvent. The aromatic solvent preferably comprises no oxygen-containing and/or nitrogen-containing, aprotic solvents (<1% by volume).

Typically, the secondary amine II is reacted with sulfuryl chloride in the substantial or complete absence of protic solvents such as water or alcohols. The proportion of water and protic organic solvents will generally not be more than 0.1% (1000 ppm) and in particular not more than 500 ppm, especially not more than 300 ppm, based on the total amount of solvent used.

Preferred aromatic compounds which are useful as aromatic solvents are, as well as benzene, alkylbenzenes such as toluene, xylenes, trimethylbenzene and ethylbenzene, and also chlorinated and/or fluorinated benzenes such as chlorobenzene, fluorobenzene and dichlorobenzenes. In a preferred embodiment, the aromatic solvent comprises chlorobenzene. In particular chlorobenzene forms the main constituent, in particular at least 80%, more preferably at least 90 or at least 95% by volume of the aromatic constituents of the aromatic solvent. In particular, chlorobenzene is the sole constituent and makes up at least 95 and especially at least 98% by volume, based on the total amount of solvent.

The reaction of the secondary amine of the formula II with sulfuryl chloride is effected preferably under temperature control and preferably at temperatures of not more than 50°

C., in particular not more than 30° C. and especially not more than 20° C. The lower limit is generally determined by the melting point of the reaction mixture and the miscibility of the reaction mixture. Frequently, the lower limit in the reaction temperature will not go below −10° C. Frequently, the reaction of the secondary amine II with sulfuryl chloride is carried out at temperatures in the range from −10 to 50° C., in particular in the range from −10 to 30° C. and especially in the range from −5 to 20° C.

For the reaction of the secondary amine of the formula II with sulfuryl chloride, the procedure will preferably be to initially charge a portion or the total amount of the solvent and sulfuryl chloride in the reaction vessel, to bring the initial charge to the desired reaction temperature and to add the secondary amine II and the tertiary amine thereto. Optionally, the secondary amine and the tertiary amine can be diluted with the solvent used for the reaction. The secondary amine II and the tertiary amine are preferably added simultaneously, especially as a mixture, such that the preferred molar ratios of secondary amine II and tertiary amine in the reaction mixture are maintained. Since the reaction of sulfuryl chloride with the tertiary amine is exothermic, secondary amine and tertiary amine are preferably added under thermal control over a prolonged period, which is typically at least 20 minutes, in particular at least 30 minutes and especially at least 60 minutes. The maximum addition time is guided by economic considerations and will generally not exceed 15 hours and in particular 8 hours. Frequently, secondary amine II and tertiary amine are added within a period of from one hour to 10 hours and especially over a period of from 2 hours to 8 hours. Optionally, the reaction can be completed by subjecting the reaction mixture, after the addition of secondary amine II and tertiary amine has ended, to a postreaction, which is typically in the range from 10 minutes to 8 hours and in particular in the range from 30 minutes to 6 hours. The total duration of addition and postreaction phase preferably will not exceed a duration of 15 hours and in particular 10 hours.

The concentration of the reactants, i.e. the total amount of sulfuryl chloride, secondary amine II and tertiary amine, is preferably from 10 to 50% by weight and in particular from 20 to 40% by weight, based on the total weight of the reaction mixture.

In this way, a reaction mixture which comprises the sulfamoyl chloride III dissolved in the solvent is obtained. In addition, the reaction mixture also comprises the salts formed in the reaction, i.e. the hydrogen chloride addition salts of the tertiary amine.

The reaction mixture thus obtained can be reacted directly with ammonia in step ii) of the process according to the invention. Preference is given, however, to removing the salts formed in the reaction by extraction, before the reaction with ammonia in step ii) is performed. The extraction is effected typically under aqueous acidic conditions, i.e. at pH<7, in particular pH<5 and especially pH<3. Preference is given to using, for the extraction, a dilute acid, especially dilute hydrochloric acid. In particular, dilute hydrochloric acid having a hydrogen chloride content in the range from 2 to 20% by weight and especially in the range from 5 to 15% by weight is used. The extraction can be effected by single or multiple treatment with the dilute aqueous acid. Preference is given to effecting the extraction at temperatures below 30° C. and especially below 20° C., for example in the range from 0 to 30° C. and especially in the range from 0 to 20° C. The aqueous phase comprising the hydrochloride of the tertiary amine is removed. Any water fractions can be removed by distillation. The distillative removal can be effected at standard pressure and is preferably carried out under reduced pressure. Optionally, aromatic solvent which has been distilled off will be replaced.

The solution of the sulfamoyl chloride of the formula III in the inert solvent thus obtained is reacted with ammonia in step ii). Optionally, the concentration of sulfamoyl chloride is adjusted by adding further inert, especially aromatic solvents. The concentration of sulfamoyl chloride in the inert solvent in step ii) will preferably be in the range from 5 to 50% by weight, in particular from 10 to 40% by weight and especially from 20 to 30% by weight.

The ammonia required for the reaction can be supplied in gaseous form or in the form of a solution, generally a nonaqueous solution. When the ammonia is supplied in the form of a solution, the solvent comprises generally less than 1% protic constituents such as water.

In a preferred embodiment of the invention, the ammonia is supplied in gaseous form. Preference is then given to performing the reaction in an ammonia atmosphere. The partial pressure of the ammonia in this ammonia atmosphere is typically in the range from 0.5 to 50 bar, in particular in the range from 1 to 30 bar and especially in the range from 2 to 20 bar. Optionally, the gaseous ammonia can be diluted with a gaseous inert, for example air, nitrogen or argon or a mixture of these gases. The ratio of the partial ammonia pressure to the total partial pressure of all inerts is, however, preferably at least 1:1, in particular at least 5:1 and especially at least 10:1. The total pressure of all gaseous constituents will generally not exceed 50 bar, in particular 30 bar and especially 20 bar. In the course of the reaction of the sulfamoyl chloride with ammonia, the partial pressure of the ammonia in the reaction vessel will be kept within the abovementioned ranges.

The reaction of the sulfamoyl chloride III with the ammonia is effected typically at temperatures in the range from 10 to 100° C., especially in the range from 30 to 80° C.

The reaction time required for the reaction is generally from 2 to 24 h, especially from 4 to 16 h.

The reaction in step ii) affords a reaction mixture which comprises the sulfuric diamide of the general formula I together with the ammonium chloride formed as a byproduct in the reaction in the inert solvent, especially the aromatic solvent. Before a further reaction, the ammonium chloride is generally removed. Since the ammonium chloride is present as a suspended solid in the inert solvent, it can in principle be removed by filtration. Preference is given to removing the ammonium chloride by means of an aqueous extraction. Preference is given to effecting the aqueous extraction at a pH of <7, in particular pH<5 and especially pH<3. Typically, a dilute aqueous acid is used for the extraction, in particular dilute aqueous hydrochloric acid and especially aqueous hydrochloric acid having a hydrogen chloride content of from 2 to 20% by weight and especially from 5 to 15% by weight. The aqueous extraction of the reaction mixture can be carried out once or more than once.

Preference is given to reextracting the combined aqueous extracts once or more than once with a suitable organic solvent in which the sulfuric diamide I is soluble, in particular an aromatic solvent and especially with the inert solvent used for the reaction, especially the aromatic solvent used for the reaction, in order to prevent yield losses. The extracted reaction mixture, optionally after combination with the reextracts, comprises the sulfuric diamide I in dissolved form with a purity sufficient for further reactions. The solution can therefore be sent to further reactions as such or after isolation of the sulfuric diamide I. Optionally, the solution of the sulfuric diamide I will be concentrated by distillation, which likewise removes any water and/or acid present in the solvent. It is also possible to isolate the sulfuric diamide from the solution thus obtained in a customary manner, for example by concentrating to dryness or by crystallization, optionally with addition of organic solvents in which the sulfuric diamide I is not soluble.

The sulfuric diamides of the general formula I thus obtained can be used especially to prepare active herbicidal ingredients of the general formula IV.

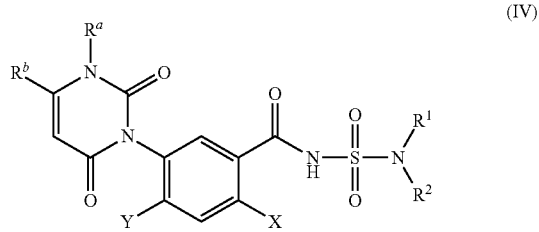

In formula, $R^1$ and $R^2$ are each as defined above. $R^a$ is hydrogen or $C_1$-$C_4$-alkyl, $R^b$ is hydrogen, $C_1$-$C_4$-alkyl or $C_1$-$C_4$-haloalkyl, X and Y are each hydrogen or halogen, where one of the X or Y radicals may also be CN.

Accordingly, the present invention further relates to the use of the process according to the invention for preparing sulfuric diamides of the formula I for the preparation of active herbicidal ingredients of the general formula IV.

The present invention further provides a process for preparing active herbicidal ingredients of the general formula IV, as described here, comprising the following steps:
a) preparation of a sulfuric diamide of the formula I by the process described here and in the claims,
b) reaction of the sulfuric diamide of the formula I with a 3-nitrobenzoyl chloride of the formula V to obtain a 3-nitrobenzenesulfonamide of the formula VI;

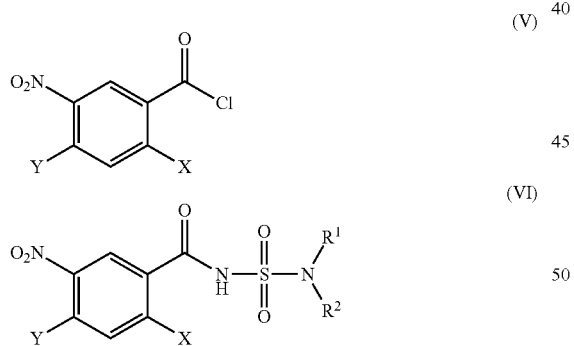

c) reduction of the 3-nitrobenzenesulfonamide of the formula VI to a 3-aminobenzenesulfonamide of the formula VII

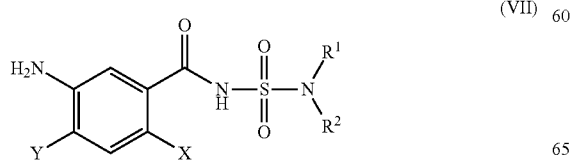

d) conversion of the 3-aminobenzenesulfonamide of the formula VII to a compound of the formula IV.

In this context, the variables $R^1$, $R^2$, X and Y used in the formulae V, VI and VII are each as defined for formula IV.

Steps b), c) and d) are known in principle from the prior art.

The reaction of the sulfuric diamide of the formula I with a nitrobenzoyl chloride of the formula V can be carried out, for example, according to scheme 2 on page 15 of WO 2004/039768, and according to the information on pages 16 to 19 or example 1 on page 56 of WO 2004/039768 or according to the examples adduced here. The disclosure on this subject of WO 2004/039768 is hereby fully incorporated by reference.

The reduction of the 3-nitrobenzenesulfonamide of the formula VI obtained in step b) to the corresponding 3-aminobenzenesulfonamide of the formula VII can likewise be carried out according to the details in WO 2004/039768 in reaction scheme 2 on page 15 and according to the information on pages 19 to 22 and 58 to 60 of WO 2004/039768, whose disclosure on this subject is hereby fully incorporated by reference. More particularly, the reduction of the compound VI to the compound VII is carried out by catalytic hydrogenation, as described on pages 21 ff. and 60 of WO 2004/039768, or according to the example of the present application.

The subsequent reaction of the 3-aminobenzenesulfonamide of the formula VII to give a compound of the formula IV is likewise known from the prior art, for example from WO 01/83459, WO 2005/054208, WO2006/010474 and WO06/125746. More particularly, the conversion can be carried out in the following manner:
reaction of the compound VII with an oxazinone by the method described in the scheme on page 37 of WO 01/83459;
by the method described in WO 2006/010474 and WO 06/125746, comprising the following steps:
d1) reaction of the 3-aminobenzenesulfonamide of the formula VII with a $C_1$-$C_4$-alkyl chloroformate to give a compound of the formula VIII

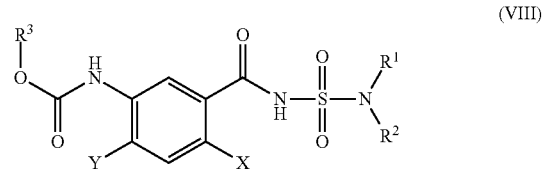

in which $R^1$, $R^2$, X and Y are each as defined for formula IV and $R^3$ is $C_1$-$C_4$-alkyl,
d2) reaction of the compound VIII with a 3-aminoacrylic ester of the formula IX

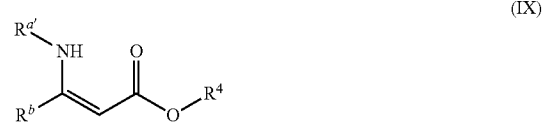

in which $R^{a'}$ is hydrogen or $C_1$-$C_4$-alkyl, $R^b$ is hydrogen, $C_1$-$C_4$-alkyl or $C_1$-$C_4$-haloalkyl and $R^4$ is $C_1$-$C_4$-alkyl.

d3) When $R^{a'}$ in formula IX is hydrogen, after step d2), an alkylation of the compound IV obtained in step d2), in which $R^a$ is hydrogen, can optionally be carried out with a compound $R^{aa}$-L in which $R^{aa}$ is $C_1$-$C_4$-alkyl and L is a nucleophilically displaceable leaving group, e.g. halogen, O—$SO_2$R or $OSO_2$—OR'(R=$C_1$-$C_4$-alkyl, phenyl or tolyl, R'=$C_1$-$C_4$-alkyl). The alkylation can be carried out by the methods described in WO 2006/010474 and WO 06/125746.

reaction of the compound VII with phosgene or diphosgene by the method described in WO 2004/039768 to obtain the corresponding isocyanate of the formula X

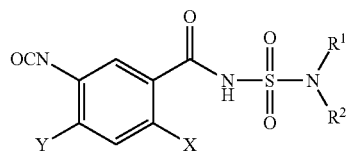

and subsequent reaction of the isocyanate X with a 3-aminoacrylic ester of the formula IX by the method described in WO 2005/054208.

The disclosure of these documents is hereby fully incorporated by reference.

The following examples serve to illustrate the invention:

EXAMPLE 1

Preparation of N-methyl-N-(1-methylethyl)aminosulfonamide (Compound I where $R^1$=methyl, $R^2$=1-methylethyl)

Step a)

A reaction vessel was initially charged under inert gas atmosphere with 137.7 g (1.0 mol) of sulfuryl chloride in 800 g of chlorobenzene and cooled to internal temperature −5° C. To this were added, over a period of 300 minutes, a mixture of 73.1 g (1.0 mol) of isopropylmethylamine and 116.3 g (1.15 mol) of triethylamine, in the course of which the temperature was kept within the range from 0 to 5° C. by cooling. After the addition had ended, the resulting suspension was stirred at 10° C. for a further 120 minutes. The suspension was then added to 250 g of 10% hydrochloric acid at 10° C. The phases were separated at 10° C. and the organic phase was washed again with 250 g of 10% aqueous hydrochloric acid at 10° C. The organic phase was removed and concentrated under reduced pressure (30 mbar, 22 to 41° C.), in order to remove water. In this way, 570 g of a solution of N-isopropyl-N-methylsulfamoyl chloride in chlorobenzene (about 25% by weight) were obtained. This corresponds to a yield of 84%.

343.4 g of the solution of N-isopropyl-N-methylsulfamoyl chloride in chlorobenzene (25% strength by weight) obtained in step i) were introduced into a pressure vessel which was flushed with nitrogen and ammonia. Subsequently, the partial pressure of the ammonia was increased to 5 bar. The reactor contents were then heated to 50° C., and this temperature was maintained for 8 hours, in the course of which an ammonia pressure of 6 bar was maintained. The suspension obtained here was added to 210 g of aqueous hydrochloric acid (8% strength), which dissolved the solids present in the reaction mixture. The pH of the aqueous phase was about 2. The phases were separated at 40° C. and the aqueous phase was extracted twice with 372 g of chlorobenzene each time. In this way, 1065 g of a 6.3% by weight solution of the title compound in chlorobenzene was obtained, which corresponds to a yield of 88%. The solution can be used directly in the subsequent reaction.

EXAMPLE 2

Preparation of 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]-benzamide Step b): (2-chloro-4-fluoro-5-nitrobenzoyl)-N'-isopropyl-N'-methylsulfamide To a solution of 43.1 g (0.277 mol) of N-methyl-N-(1-methylethyl)sulfamoylamide and 0.77 g (12.0 mmol) of tributylmethylammonium chloride in 637 g of chlorobenzene were added, at 20° C. within 60 min, 43.7 g (50% strength in water) of NaOH. 15 minutes after the start of addition of the base, 65.0 g (0.26 mol) of 2-chloro-4-fluoro-3-nitrobenzoyl chloride in 70 g of chlorobenzene were added within 45 min. Both metered additions ended simultaneously. The reaction mixture was subsequently stirred at 20° C. for 1 h and diluted by means of addition of 424 g of water and 138 g of isohexane. The aqueous phase was acidified to pH 4.5 with concentrated hydrochloric acid and then removed at 68-70° C. The organic phase was admixed with 430 g of water and 60 g of isohexane and the phases were separated again at pH 4.5 while hot. The resulting organic phase was admixed with a further 280 g of isohexane and then cooled to 5° C. After filtration, washing with water and drying at 70° C. under reduced pressure, 82.1 g (87% of theory, purity 97%) of N-(2-chloro-4-fluoro-5-nitrobenzoyl)-N'-isopropyl-N'-methylsulfamide were obtained.

$^1$H NMR (400 MHz, CDCl$_3$) δ=9.1 ppm (s, NH), 8.4 (d, Ar—H), 7.45 (d, Ar—H), 4.25 (sept., iso-Pr-H), 2.95 (s, Me), 1.25 (d, iso-Pr-H). iso-Pr=isopropyl=1-methylethyl Step c): N-(2-chloro-4-fluoro-5-aminobenzoyl)-N'-isopropyl-N'-methylsulfamide 177 g (0.500 mol; 99.9%) of N-(2-chloro-4-fluoro-3-nitrobenzoyl)-N'-isopropyl-N'-methylsulfamide were admixed in 397 g of methanol with 2.17 g (0.008 mol %) of 1% Pt/C (63% suspension in water). The mixture was hydrogenated with 5 bar of hydrogen at 60-70° C. with stirring. After 2 h, the solution was decompressed, the reaction mixture was filtered at 60° C. and the solvent was removed by distillation. 157.8 g (97.5% of theory, purity: 99%) of N-(2-chloro-4-fluoro-5-aminobenzoyl)-N'-isopropyl-N'-methylsulfamide were obtained as a white-yellowish solid (m.p.: 147-149° C.).

$^1$H NMR (400 MHz, d-DMSO) δ=11.9 ppm (s, NH), 7.35 (d, Ar—H), 6.90 (d, Ar—H), 5.50 (br. s., NH$_2$), 4.05 (sept., iso-Pr-H), 2.80 (s, Me), 1.15 (d, iso-Pr-H).

Step d1): N-[2-chloro-4-fluoro-5-{(ethoxycarbonyl)amino}benzoyl]-N'-isopropyl-N'-methylsulfamide (Variant 1)

To a solution of 50.0 g (0.153 mol; 99.3%) of N-(2-chloro-4-fluoro-5-aminobenzoyl)-N'-isopropyl-N'-methylsulfamide in 225 g of toluene were added, at 105-110° C., 22.7 g (0.207 mol) of ethyl chloroformate and the mixture was subsequently stirred at 108-110° C. for 6.5 h. The reaction mixture was concentrated to dryness on a rotary evaporator under reduced pressure. After drying under reduced pressure at 70° C., 59.9 g (98.4% of theory, purity 99.7%) of N-[2-chloro-4-fluoro-5-{(ethoxycarbonyl)-amino}benzoyl]-N'-isopropyl-N'-methylsulfamide were obtained.

$^1$H NMR (400 MHz, CDCl$_3$) δ=8.9 ppm (s, NH), 8.4 (d, Ar—H), 7.2 (d, Ar—H), 6.80 (s, NH), 4.30-4.20 (m, iso-Pr-H, CH$_2$O), 2.95 (s, Me), 1.40 (q, CH$_3$CH$_2$O), 1.25 (d, iso-Pr-H).

Step d1): N-[2-chloro-4-fluoro-5-{(ethoxycarbonyl) amino}benzoyl]-N'-isopropyl-N'-methylsulfamide (Variant 2)

To a solution of 50.0 g (0.153 mol; 99.3%) of N-(2-chloro-4-fluoro-5-aminobenzoyl)-N'-isopropyl-N'-methylsulfamide in 450 g of toluene were added, at 105-110° C., 26.9 g (0.245 mol) of ethyl chloroformate and the mixture was then stirred at 108-110° C. for 6.5 h. The reaction mixture was concentrated to dryness on a rotary evaporator under reduced pressure. After drying under reduced pressure at 70° C., 61.2 g (99.3% of theory, purity 98.4%) of N-[2-chloro-4-fluoro-5-{(ethoxycarbonyl)amino}benzoyl]-N'-isopropyl-N'-methylsulfamide were obtained.

Step d2): 2-chloro-5-[3,6-dihydro-2,6-dioxo-4-(trifluoromethyl)-1(2H)-pyrimidinyl]-4-fluoro-N-{[methyl-(1-methylethyl)amino]sulfonyl}benzamide 396 g (1 mol) of N-(2-chloro-4-fluoro-5-[(ethoxycarbonyl)amino]benzoyl)-N'-isopropyl-N'-methylsulfamide were dissolved at room temperature in 1583 g of DMF (=dimethylformamide), and 189 g (1.02 mol) of ethyl 3-amino-4,4,4-trifluoro-2-butenoate were added. 378 g (2.1 mol) of sodium methoxide solution (30% in methanol) were metered in at 115-120° C. within 4 h, and methanol and ethanol were distilled off during this time. The mixture was left to stir for a further 30 min. For workup, the reaction mixture was metered with cooling into dilute sulfuric acid, and, after the end of the addition, the reaction mixture had a pH of <2 and the title compound precipitated out as a solid. The precipitated product was filtered off, washed with water and dried. 433 g (89% of theory) of the title compound were obtained [m.p. 238° C. (decomposition)].

Step d3): 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl] benzamide 40.0 g (0.0785 mol) of 2-chloro-5-[3,6-dihydro-2,6-dioxo-4-(trifluoromethyl)-1(2H)-pyrimidinyl]-4-fluoro-N-{[methyl-(1-methylethyl)amino]sulfonyl}benzamide, 2.5 g (0.0078 mol) of tetrabutylammonium bromide (=TBAB) and 13.4 g (0.106 mol) of dimethyl sulfate were initially charged at 25° C. in a mixture of toluene, water and THF (=tetrahydrofuran), and the mixture was heated to 40° C. Subsequently, by adding aqueous 10% NaOH solution, a pH of 5.3-5.5 was established in the reaction mixture. The mixture was stirred at 40° C. for 1 h, in the course of which 10% aqueous NaOH solution continued to be added, such that the pH was constant at the pH established beforehand. After 1 h, the addition of the aqueous 10% NaOH solution was stopped, whereupon the pH fell to 4.4-4.5. The mixture was left to stir at a pH of 4.4-4.5 and 40° C. for a further 5.5 h. After the reaction had ended, the phases were separated, the organic phase was dried and the solvent was partly removed. In the course of cooling, the title compound crystallizes out, and is filtered off, washed with toluene and dried (33 g, 84%).

EXAMPLE 3

Preparation of 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]-benzamide (Variant with Performance of Steps c) and d1) without Intermediate Isolation)

The preparation was effected analogously to the method for example 2, with the difference that steps c) and d1) were carried out as follows:

179 g (0.500 mol; 99%) of N-(2-chloro-4-fluoro-3-nitrobenzoyl)-N'-isopropyl-N'-methylsulfamide were admixed in 391 g of methanol with 4.08 g (0.015 mol %) of 1% Pt/C (63% water) and hydrogenated with 5 bar of hydrogen at 60-70° C. with stirring. After 2 h, the solution was decompressed, the reaction mixture was filtered at 60° C. and the solution was admixed with 2200 g of toluene. The methanol was removed by distillation together with the water of reaction at 65-68° C. while gradually lowering the pressure from 900 mbar to 250 mbar. Subsequently, the suspension of N-(2-chloro-4-fluoro-5-aminobenzoyl)-N'-isopropyl-N'-methylsulfamide in toluene was heated to 106-107° C. and admixed with 64.4 g (0.588 mol) of ethyl chloroformate within 10 min. The mixture was subsequently stirred at 110° C. for 6.5 h. Subsequently, 746 g of toluene were distilled off at standard pressure and the mixture was then cooled to internal temperature 5° C. After the product solution had been seeded with 150 mg of the target compound, the product crystallized at 5° C. within 60 min. After filtration and drying under reduced pressure at 70° C., 166.2 g (95.0% of theory, purity 98.5%) of N-[2-chloro-4-fluoro-5-{(ethoxycarbonyl)amino}benzoyl]amino}benzoyl]-N'-isopropyl-N'-methylsulfamide were obtained.

EXAMPLE 4

Preparation of 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]-benzamide (Variant with Crystallization of the Product Obtained in d1))

The preparation was effected analogously to the method for example 2, with the difference that step d1) was carried out as follows:

To a solution of 150.9 g (0.466 mol) of N-(2-chloro-4-fluoro-5-aminobenzoyl)-N'-isopropyl-N'-methylsulfamide in 350 g of methanol and 18.4 g of water were added 1100 g of toluene. The methanol was removed by distillation together with the water at 65-68° C. while gradually lowering the pressure from 900 mbar to 250 mbar. Subsequently, the suspension of N-(2-chloro-4-fluoro-5-aminobenzoyl)-N'-isopropyl-N'-methylsulfamide in toluene was heated to 108-109° C., then admixed with 64.4 g (0.588 mol) of ethyl chloroformate within 10 min and subsequently stirred at 110° C. for 6.5 h. After the product solution had been seeded with 100 mg of the target compound, the product crystallized at 5° C. within 60 min. After filtration and drying at 70° C. under reduced pressure, 169.6 g (92.0% of theory, purity 99.7%) of N-[2-chloro-4-fluoro-5-{(ethoxycarbonyl)amino}benzoyl]amino}benzoyl]-N'-isopropyl-N'-methyl-sulfamide were obtained.

The invention claimed is:

1. A process for preparing a sulfuric diamide of the formula (I)

in which $R^1$ and $R^2$ are each independently a primary alkyl radical having from 1 to 8 carbon atoms, a secondary alkyl radical having from 3 to 8 carbon atoms or a cycloalkyl radical having from 5 to 8 carbon atoms, comprising i) reacting a secondary amine of the formula (II)

$$R^1R^2NH \quad (II)$$

with sulfuryl chloride in an inert organic solvent in the presence of a tertiary amine to give a sulfamoyl chloride of the formula (III)

wherein the tertiary amine is present in amount of from 1.05 to 1.5 equivalents, based on the secondary amine of formula (II); and wherein the secondary amine of the formula (II) and sulfuryl chloride are used in a molar ratio of from 1:1.1 to 1.1:1; and ii) reacting the sulfamoyl chloride of the formula (III) obtained in step i) with gaseous ammonia, wherein the reaction is performed at temperatures in the range of from 30 to 80° C., the sulfamoyl chloride of the formula (III) being used in step ii) in the form of the solution obtained in step i) in the inert organic solvent.

2. The process according to claim 1, wherein step i) comprises an extractive removal of the salts formed in the reaction.

3. The process according to claim 1, wherein the tertiary amine is a tri-$C_1$-$C_6$-alkylamine.

4. The process according to claim 1, wherein the $R^1$ radical in the formulae (I), (II) and (III) is a primary alkyl radical having from 1 to 8 carbon atoms or a secondary alkyl radical having from 3 to 8 carbon atoms and the $R^2$ radical is a secondary alkyl radical having from 3 to 8 carbon atoms.

5. The process according to claim 4, wherein the secondary amine of the formula (II) is N-(1-methylethyl)-N-methylamine.

6. The process according to claim 1, wherein the inert organic solvent is an aromatic solvent.

7. The process according to claim 6, wherein the aromatic solvent comprises chlorobenzene.

8. A process for preparing active herbicidal ingredients of the general formula (IV)

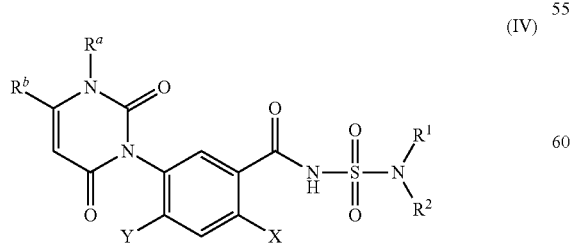

in which $R^1$ and $R^2$ are each as defined in claim 1, $R^a$ is hydrogen or $C_1$-$C_4$-alkyl, $R^b$ is hydrogen, $C_1$-$C_4$-alkyl or $C_1$-$C_4$-haloalkyl, X and Y are each hydrogen or halogen, where one of the X or Y radicals may also be CN, comprising a) preparing the sulfuric diamide of the formula I by the process according to claim 1, b) reacting the sulfuric diamide of the formula (I) with a 3-nitrobenzoyl chloride of the formula (V) to obtain a 3-nitrobenzenesulfonamide of the formula (VI);

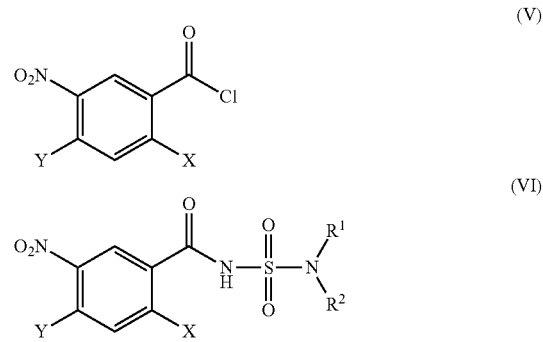

c) reducing the 3-nitrobenzenesulfonamide of the formula (VI) to a 3-aminobenzenesulfonamide of the formula (VII)

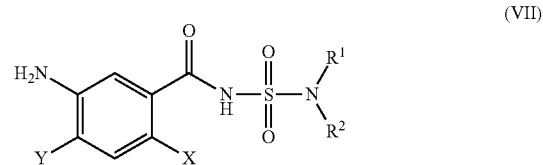

d) converting the 3-aminobenzenesulfonamide of the formula (VII) to a compound of the formula (IV).

9. The process according to claim 8, wherein step d) comprises:

d1) reacting the 3-aminobenzenesulfonamide of the formula (VII) with a $C_1$-$C_4$-alkyl chloroformate to give a compound of the formula (VIII)

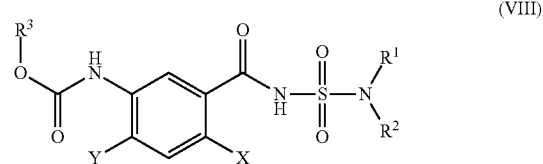

in which $R^1$, $R^2$, X and Y are each as defined for formula (IV) and $R^3$ is $C_1$-$C_4$-alkyl, d2) reacting the compound (VIII) with a 3-aminoacrylic ester of the formula (IX)

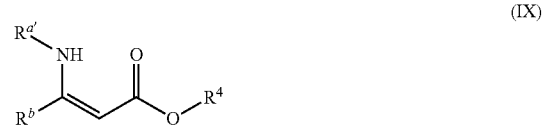

in which $R^{a'}$ is hydrogen or $C_1$-$C_4$-alkyl, $R^b$ is hydrogen, $C_1$-$C_4$-alkyl or $C_1$-$C_4$-haloalkyl and $R^4$ is $C_1$-$C_4$-alkyl, and d3) when $R^{a'}$ is hydrogen, optional alkylation of the compound IV obtained in step d2), in which $R^a$ is hydrogen, with a compound $R^{aa}$-L in which $R^{aa}$ is $C_1$-$C_4$-alkyl and L is a nucleophilically displaceable leaving group, to obtain a compound of the general formula (IV).

\* \* \* \* \*